United States Patent [19]

Klessing et al.

[11] 4,364,953

[45] Dec. 21, 1982

[54] 2-0- AND 5-0-SUBSTITUTED 1.4;3.6-DIANHYDROHEXITOL MONONITRATES AND PHARMACEUTICAL COMPOSITION

[75] Inventors: Klaus Klessing, Ettlingen; Shyam S. Chatterjee, Karlsruhe, both of Fed. Rep. of Germany

[73] Assignee: Firma Willmar Schwabe, Karlsruhe, Fed. Rep. of Germany

[21] Appl. No.: 285,407

[22] Filed: Jul. 20, 1981

[30] Foreign Application Priority Data

Jul. 25, 1980 [DE] Fed. Rep. of Germany ....... 3028289

[51] Int. Cl.³ ................. A61K 31/34; A61K 31/455; C07D 493/04
[52] U.S. Cl. .................................. 424/266; 424/285; 546/270; 549/464
[58] Field of Search .......................... 260/347.2, 347.8; 546/270; 424/266, 285; 549/464

[56] References Cited

U.S. PATENT DOCUMENTS 3,886,186  5/1975  Dvonch et al. ................. 260/347.8

Primary Examiner—Richard Raymond
Attorney, Agent, or Firm—Toren, McGeady & Stanger

[57] ABSTRACT 2-0- and 5-0-substituted 1.4;3.6-dianhydrohexitol mononitrates of the general formula I,

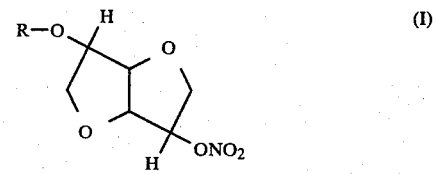

wherein R is a halogen-substituted phenyl group, a methanesulphonyl or nicotinoyl group, as well as their physiologically acceptable acid-addition salts, insofar as R signifies the nicotinoyl group.

Processes for the preparation of said compounds and pharmaceutical compositions containing said compounds.

14 Claims, No Drawings

2-O- AND 5-O-SUBSTITUTED 1.4;3.6-DIANHYDROHEXITOL MONONITRATES AND PHARMACEUTICAL COMPOSITION

BACKGROUND OF THE INVENTION

1. Field of the Invention

The invention concerns 2-O- and 5-O-substituted 1.4;3.6-dianhydrohexitol mononitrates of the general formula I,

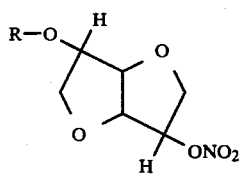

wherein R is a halogen-substituted phenyl group, a methanesulphonyl or nicotinoyl group, as well as their physiologically acceptable acid-addition salts, insofar as R signifies the nicotinoyl group.

The basic structure of these compounds consists of the stereoisomeric 1.4;3.6-dianhydrohexitols which can be converted into one another by epimerisation, namely, either 1.4;3.6-dianhydro-L-iditol (= "isoidide") (II),

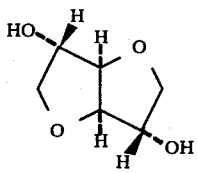

in which the OH groups in the 2- and 5-position each have the exo configuration, or 1.4;3.6-dianhydro-D-glucitol (= "isosorbide") (III),

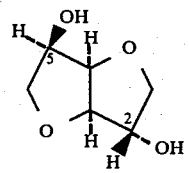

which has a 2-exo-standing and a 5-endo-standing OH group and thus—in the case of different substituents in the 2- and 5-position—occurs in two isomeric forms.

Finally, the basic structure of some compounds consists of 1.4;3.6-dianhydro-D-mannitol (= "isomannide") (IV),

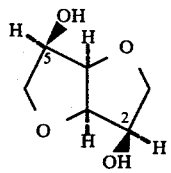

which has two endo-standing OH groups.

Since, in contradistinction to the glucitol derivatives, in the case of the iditol and mannitol derivatives a differentiation between the 2- and 5-substituents is not possible because the $C^2$-atom, in the case of rotation of the molecule through 180°, becomes the $C^5$-atom, references to the 5-position or 2-position of substituents are, in the case of these derivatives, superfluous. However, for a better comparison of the structures of the individual compounds with the general formulae, the isoidide derivatives are here referred to as 5-O-position-substituted isoidide derivatives since they can be prepared by nucleophilic substitution, with reversal of configuration, for example from 5-O-alkylsulphonyl- or 5-O-arylsulphonyl-isosorbide.

2. Description of the Prior Art

A brief survey of the stereoisomerism of the 1.4;3.6-dianhydrohexitols is given by J. A. Mills in Advances in Carbohydrate Chem., 10, 1–53 (1955).

The invention also concerns processes for the preparation of the initially mentioned 2-O - and 5-O-substituted 1.4;3.6-dianhydrohexitol mononitrates, as well as pharmaceutical compositions which contain the compounds according to the invention.

The nitrates of 1.4;3.6-dianhydro-D-glucitol (also called 1.4;3.6-dianhydro-D-sorbitol) are known e.g. from U.S. Pat. No. 3,886,186, namely, not only the 2- and 5-mononitrates but also the 2,5-dinitrate of isosorbide. These nitrates, especially the dinitrate, which is already commercially available as a medicament, are pharmacologically active substances with haemodynamic, vasodialatory and antianginous effectiveness which are especially employed in the case of coronary insufficiency and for the treatment of angina pectoris.

Furthermore, from U.S. Pat. No. 3,886,186 there are also known the 5-acetate-2-nitrate, 2-acetate-5-nitrate, 2-ethylate-5-nitrate, 5-nitrate-2-sulphamate, 2-carbamate-5-nitrate and the 5-carbamate-2-nitrate of isosorbide, as well as the corresponding propionate, butyrate, isobutyrate, caproate and benzoate mononitrates.

Furthermore, the p-toluenesulphonic acid esters of the mononitrates of isoidide, isosorbide and isomannide are known (Can. J. Chem., 45, 2191–2194 (1967)). However, only the infra-red spectra of these compounds have hitherto been described in detail. On the other hand, nothing has become known regarding the pharmacological properties of the compounds.

The pharmacokinetics of the dinitrate and mononitrates of isosorbide, isomannide and isoidide have been described by Bogaert and Rosseel in Naunyn-Schmiedeberg's Arch. Pharmacol., 275, 339 (1972).

However, it has been shown that the nitrates cause unpleasant side effects, especially headaches. Furthermore, the mononitrates are more poorly resorbed than, for example, isosorbide dinitrate (ISDN). In addition, the dinitrates of isosorbide, isomannide and isoidide can only be prepared and handled with special precautionary measures since they are explosive.

SUMMARY OF THE INVENTION

Thus, a need existed for the making available of new pharmaceutical agents with the same spectrum of activity but which do not display the mentioned disadvantages and for the provision of new 1.4;3.6-dianhydrohexitol mononitrates which can be used as effective components of such pharmaceutical agents.

The task forming the basis of the invention consists in satisfying the stated need, the solution of this problem in making available the substances according to the invention.

Thus, the subject of the invention are 5-O-substituted 1.4;3.6-dianhydro-L-iditol 2-nitrates of the general formula V,

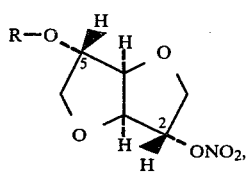

(V)

5-O-substituted 1.4;3.6-dianhydro-D-glucitol 2-nitrates of the general formula VI,

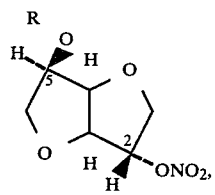

(VI)

2-O-substituted 1.4;3.6-dianhydro-D-glucitol 5-nitrates of the general formula VII,

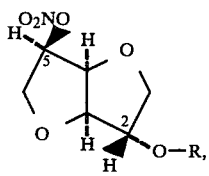

(VII)

as well as 5-O-substituted 1.4;3.6-dianhydro-D-mannitol 2-nitrates of the general formula VIII,

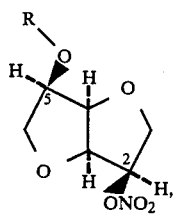

(VIII)

wherein R in each case signifies either a halogen-substituted phenyl group, a methanesulphonyl or a nicotinoyl group, as well as their physiologically acceptable acid-addition salts, insofar as R signifies the nicotinoyl group.

The compounds according to the invention possess coronary flowthrough-increasing, spasmolytic, blood pressure-lowering, negatively inotropic and heart frequency-lowering effectiveness. They are suitable for the treatment of coronary diseases, for the treatment and prophylaxis of angina pectoric attacks, for the post-treatment of heart infarcts and for the treatment of heart insufficiencies. The new compounds possess a good therapeutic range. The oral absorption is especially good and the period of action long. Furthermore, they bring about an improvement of the peripheral blood flow and of the brain blood flow.

The handling and preparation of the compounds according to the invention is much less dangerous than, for example, in the case of the known ISDN because they are not explosive.

In the 1.4;3.6-dianhydrohexitol basic structure, the compounds according to the invention possess 4 asymmetrical C-atoms and are present in optically-active form since, as starting compounds, there are used optically pure 1.4;3.6-dianhydrohexitols, which are easily obtainable from naturally-occurring sugar alcohols.

The compounds according to the invention can be prepared starting from the epimeric, unsubstituted 1.4;3.6-dianhydrohexitols, thus starting from L-isoidide, D-isosorbide and D-isomannide, namely, by various synthesis routes:

The first route according to the invention for the preparation of those compounds according to the invention of general formula I, wherein R signifies the methanesulphonyl or nicotinoyl radical, consists in that the corresponding 1.4;3.6-dianhydrohexitol is esterified with nitric acid, nitrating acid or with a mixture of nitric acid and acetic anhydride/acetic acid, possibly in the presence of urea, whereby, in each case, a mixture of the corresponding mononitrate or mononitrates and of the dinitrate result. In order to keep the proportion of dinitrate as low as possible, one thereby preferably selects the ratio between nitric acid and isohexide in such a manner that, for 1 mol isohexide, there are used 0.5 to 1 mol nitric acid. The mixture of the mono- and dinitrates is taken up in ether and extracted with water, whereby the mononitrate can be isolated from the aqueous phase, whereas the undesired dinitrate remains completely in the ether phase. In the case of the esterification to the isosorbide nitrates, it is advantageous to carry out the separation of the reaction products by column chromatography on silica gel, whereby not only is the dinitrate completely separated but also a separation of the two mononitrates takes place, namely, of the isosorbide 5(endo)-nitrate and of the isosorbide 2(exo)nitrate.

The corresponding 1.4;3.6-dianhydrohexitol mononitrate is subsequently reacted with the desired acid chloride (methanesulphonic acid chloride or nicotinic acid chloride) to give the desired compound. According to this first process, for example, 1.4;3.6-dianhydro-L-iditol is esterified with nitric acid and the resultant 1.4;3.6-dianhydro-L-iditol 2-nitrate reacted with nicotinic acid chloride to give 1.4;3.6-dianhydro-L-iditol 2-nitrate 5-nicotinate.

The second process according to the invention for the preparation of those compounds of general formula I, wherein R signifies the methanesulphonyl or the nicotinoyl radical, consists in that the corresponding 1.4;3.6-dianhydrohexitol is first reacted with the desired acid chloride (methanesulphonic acid chloride or nicotinic acid chloride), whereby, in each case, a mixture of the corresponding di- and monoesters results, which is separated by fractional crystallisation, fractional extraction or with the help of other per se known methods. The desired monoacylate is subsequently esterified with nitric acid to give the desired compound.

According to this second process according to the invention, starting, for example, from 1.4;3.6-dianhydro-D-glucitol, by reaction with methanesulphonic acid chloride there is first prepared 1.4;3.6-dianhydro-D-glucitol 5-methanesulphonate and the latter reacted with nitric acid, nitrating acid or with a mixture of nitric acid, glacial acetic acid and acetic anhydride to give 1.4;3.6-dianhydro-D-glucitol 2-nitrate 5-methanesulphonate.

DESCRIPTION OF THE PREFERRED EMBODIMENT

For the preparation of those compounds according to the invention of general formula I, wherein R signifies a halophenyl radical, one first prepares a reactive isohexide monoacylate, preferably—corresponding to the above-described process—an isohexide monomethanesulphonate or toluenesulphonate, and reacts this with a suitable salt of the desired halophenol, for example with p-chlorophenol sodium salt, which can also be produced in the course of the reaction in situ by the addition of a suitable proton acceptor to the corresponding halophenol, for example by the addition of sodium hydride, to give the desired halophenyl ether. The so prepared halophenyl ether of the isohexide is subsequently, as previously described, esterified with nitric acid to give the mononitrate, preferably at temperatures below 0° C. in order to avoid a nitration of the halophenyl radical.

The etherification is preferably carried out in a dipolar, aprotic solvent, e.g. in dimethyl sulphoxide or in glycol diethers, at elevated temperature and takes place according to the manner of reaction of a typical bimolecular nucleophilic substitution ($S_N2$ reaction), which always involves a reversal of the configuration on the central carbon atom. This reversal of configuration, which is also known to the expert by the terms "inversion" or "Walden inversion", is the reason why, from the 1.4;3.6-dianhydro-D-glucitol 5-acyl derivative, in which the acyl radical is present endo-standing in the 5-position, the corresponding etherified 1.4;3.6-dianhydro-L-iditol derivative always results in which the newly introduced halophenyl ether group no longer stands in the endo- but rather in the exo-position. The Walden inversion involving the $S_N2$ reaction is, in completely corresponding manner, responsible for the fact that from the corresponding 1.4;3.6-dianhydro-L-iditol acylate there results the 1.4;3.6-dianhydro-D-glucitol ether endo-substituted in the 5-position, from the 1.4;3.6-dianhydro-D-mannitol acylate the corresponding 1.4;3.6-dianhydro-D-glucitol ether exo-substituted in the 2-position and from the 1.4;3.6-dianhydro-D-glucitol 2-exo-acylate the corresponding 1.4;3.6-dianhydro-D-mannitol ether endo-substituted in the 2-position.

According to the third process according to the invention, those compounds of general formulae V and VII according to the invention can also be prepared, wherein R signifies the nicotinoyl radical and thereby the nicotinic acid residue takes up the 2(exo)- or 5(exo)-position of the corresponding isosorbide or isoidide nitrate, in that one subjects the corresponding isohexide methanesulphonate with endo-standing methanesulphonyl group to the nucleophilic $S_N2$ substitution by suitable salts of nicotinic acid, for example sodium nicotinate, in a dipolar aprotic solvent, for example dimethylformamide, at elevated temperature. Here, too, reversal of configuration takes place at the point of substitution but the nucleophilic force of the nicotinate anion is no longer sufficient in order also to substitute the sterically more strongly hindered isohexide exomethanesulphonates.

The so prepared isohexide nicotinates are—as previously described—esterified with nitric acid to give the isohexide nicotinate nitrates. In this manner, for example, 1.4;3.6-dianhydro-D-glucitol 5-methane-sulphonate can be reacted with sodium nicotinate in dimethylformamide at 150° C. to give 1.4;3.6-dianhydro-L-iditol 5-nicotinate, which is subsequently esterified with nitric acid to give 1.4;3.6-dianhydro-L-iditol 5-nicotinate 2-nitrate.

In order to convert those compounds according to the invention of general formula I, wherein R signifies the nicotinoyl radical, into their physiologically acceptable salts, there can be used inorganic acids and mineral acids, such as hydrohalic acids and phosphoric acid, as well as organic acids, such as carboxylic and sulphonic acids, for example malonic, succinic, lactic, tartaric, malic, benzoic, salicylic, citric, ascorbic, nicotinic or p-toluenesulphonic acid. The free bases can again be liberated from the acid-addition salts by careful treatment with bases, for example sodium or potassium hydrogen carbonate.

The subject of the invention are, furthermore, pharmaceutical compositions which, besides the usual carrier and addition materials, contain at least one of the compounds according to the invention or of their physiologically acceptable salts. These compositions can be used as medicaments in human and veterinary medicine. Conventional carrier materials are, for example, water, vegetable oils, polyethylene glycols, glycerol esters, gelatine, carbohydrates, such as lactose or starch, magnesium stearate, talc, Vaseline. Conventional additive materials are, for example, preserving, stabilising, lubricating, wetting agents, emulsifiers, physiologically acceptable salts, buffer substances, colouring, flavouring and aroma materials. The selection of the carrier and additive materials depends upon whether the compounds according to the invention are to be administered enterally, parenterally or topically.

The compounds according to the invention can also be administered in admixture with other active materials, for example vitamins or known commercially available heart-circulation agents, especially also with $\beta$-receptor blockers.

EXAMPLE OF A PHARMACEUTICAL COMPOSITION

For the preparation of tablets each of 100 mg. individual weight which each contain 5 mg. of active material, one requires I. 5 g. 1.4;3.6-dianhydro-D-glucitol 2-nitrate 5-nicotinate
II. 54 g. microcrystalline cellulose
III. 20 g. lactose
IV. 20 g. maize starch
V. 0.5 g. colloidal silicic acid
VI. 0.5 g. magnesium stearate The substances I–IV are dry mixed for 10 min., subsequently the mixture is added to the substances V and VI, one mixes for a further 10 minutes and presses the so obtained powder on a tabletting machine to tablets of 100 mg. individual weight.

Each of the compounds and intermediate products according to the invention mentioned in the following Examples represents an especially suitable agent for the preparation of pharmaceutical compositions.

The abbreviations contained in the Examples have the following meanings:

m.p. = melting point (uncorrected)
(decomp.) = decomposition
d = density
$[\alpha]_D^{25}$ = optical rotation at 25° C., sodium D line After the optical rotational values are given the concentrations of the measured solutions, whereby c 2, for example, signifies a concentration of 2 g./100 ml. of

EXAMPLE NO. 1

5-O-(4-Chlorophenyl)-1.4;3.6-dianhydro-L-iditol 2-nitrate:

(a) 1.4;3.6-Dianhydro-D-glucitol 2-methanesulphonate, 5-methanesulphonate and 2,5-dimethanesulphonate:

To a solution of 4.82 kg. (33 mol) 1.4;3.6-dianhydro-D-glucitol in 24 litres pyridine one adds dropwise, with the exclusion of moisture, stirring and cooling to −15° to −20°, within the course of several hours, 3.1 liters (40 mol) methanesulphonic acid chloride. One subsequently further stirs for 15 hours without cooling. One distils off the pyridine in vacuo, adds the oily residue to 15 liters of water, boils up and allows to cool. Suction filtration, washing with 4 liters of water and drying of the crystalline precipitate gives 2.22 kg. (7.34 mol) 1.4;3.6-dianhydro-D-glucitol 2,5-dimethanesulphonate. The filtrate is neutralised, with stirring and water cooling, with about 1.5 kg. sodium hydroxide and evaporated to dryness in a vacuum at about 70°. The dry residue is continuously hot extracted with a total of 30 liters of chloroform and the extract hot filtered. One leaves the extract to stand for 15 hours at 20°, filters off the crystalline precipitate with suction, washes it twice with 2 liter amounts of chloroform, dries and obtains 2.3 kg. (10.26 mol) 1.4;3.6-dianhydro-D-glucitol 5-methanesulphonate. The combined filtrates are evaporated in a vacuum and the residue dissolved hot in 22 liters ethanol. One leaves to stand for 15 hours at 20°, filters off the crystalline precipitate with suction, washes it twice with 3 liter amounts of ethanol, dries and obtains 0.65 kg. (2.90 mol) 1.4;3.6-dianhydro-D-glucitol 2-methanesulphonate. Evaporation of the filtrates gives 2.21 kg. (9.85 mol) of a mixture of the two isomeric monomethanesulphonates which, according to need, can be further separated by repetition of the alternating crystallisations from chloroform and ethanol or, by esterification with methanesulphonic acid chloride in pyridine, is completely converted into 1.4;3.6-dianhydro-D-glucitol 2,5-dimethanesulphonate.

Analytical amounts of the methanesulphonates give, after recrystallisation, correct elementary analyses and the melting points and optical rotations set out in Table 1:

TABLE 1

| 1.4;3.6-dianhydro-D-glucitol | recrystallised from | m.p. [°C.] | $[\alpha]_D^{25}$ |
|---|---|---|---|
| 2-methane-sulphonate | chloroform | 135–138.5 | 62.5 (c 2; acetone) |
| 5-methane-sulphonate | chloroform | 123–124 | 75.9 (c 2; methanol) |
| 2,5-dimethane-sulphonate | ethanol/acetone | 127–128 | 74 (c 2; acetone) |

Remark:

If one reacts 1.4;3.6-dianhydro-D-glucitol with the 2 to 2.5 fold molar amount of methanesulphonic acid chloride under the same reaction conditions, one obtains 1.4;3.6-dianhydro-D-glucitol 2,5-dimethanesulphonate in almost quantitative yield.

(b) 5-O-(4-Chlorophenyl)-1.4;3.6-dianhydro-L-iditol:

To a solution of 13.0 g. 4-chlorophenol (0.1 mol) in 70 ml. anhydrous dimethyl sulphoxide (DMSO) are added portionwise 2.4 g. sodium hydride (0.1 mol). With stirring and exclusion of moisture, one heats to 80° and allows a solution of 11.2 g. (0.05 mol) 1.4;3.6-dianhydro-D-glucitol 5-methanesulphonate in 30 ml. anhydrous DMSO to drop in. After stirring for 24 hrs. at 80°, one cools, adds water dropwise for the hydrolysis of unreacted sodium hydride and subsequently 100 ml. water and 200 ml chloroform. One stirs up thoroughly, separates off the chloroform phase, shakes it out successively with 200 ml. water, 100 ml. 1 molar aqueous sodium hydroxide solution and 200 ml. water, dries over anhydrous sodium sulphate and evaporates in a vacuum. Recrystallisation of the residue from chloroform/ether gives 11.5 g. (45 mmol) 5-O-(4-chlorophenyl)-1.4;3.6-dianhydro-L-iditol.

M.p. 107°–110°; $[\alpha]_D^{25}$ 17.0 (c 2; chloroform)

Elementary analysis: $C_{12}H_{13}ClO_4$ (256.68) calc.: C, (56.15); H, (5.10); Cl, (13.81). found: C, (55.97); H, (5.07); Cl, (13.9).

(c) 5-O-(4-Chlorophenyl)-1.4;3.6-dianhydro-L-iditol 2-nitrate:

To a solution of 13 g. (50 mmol) 5-O-(4-chlorophenyl)-1.4;3.6-dianhydro-L-iditol in 150 ml. acetic acid and 35 ml. acetic anhydride one adds dropwise, with stirring and cooling to 10°, a solution of 3.5 ml. 65% nitric acid in 50 ml. glacial acetic acid and 12.5 ml. acetic anhydride within 1 hr. and stirs overnight with gradual warming up to room temperature. One adds 250 ml. each of chloroform and water thereto, stirs up, separates off the chloroform phase, washes it with 250 ml. water and, after drying over anhydrous sodium sulphate, evaporates it under reduced pressure. Recrystallisation of the oily residue from ethanol gives 13.3 g. (44 mmol) 5-O-(4-chlorophenyl)-1.4;3.6-dianhydro-L-iditol 2-nitrate.

M.p. 76°–77°; $[\alpha]_D^{25}$ 41.4 (c 2; chloroform)

Elementary analysis: $C_{12}H_{12}ClNO_6$ (301.69): calc.: C, (47.77); H, (4.04); N, (4.64); Cl, (11.76). found: C, (47.97), H, (4.03); N, (4.38); Cl, (11.9).

EXAMPLE NO. 2

1.4;3.6-Dianhydro-L-iditol 2-nitrate 5-nicotinate:

(a) 1.4;3.6-Dianhydro-L-iditol 2-nitrate:

To a solution of 62 g. (0.42 mol) 1.4;3.6-dianhydro-L-iditol in 800 ml. acetic acid and 280 ml. acetic anhydride one adds dropwise, with stirring and cooling to 8°–10°, a mixture of 18.5 g. (0.42 mol) 95% nitric acid (d=1.5), 400 ml. acetic acid and 100 ml. acetic anhydride and then stirs for 12 hrs. One dilutes with 3.5 litres of water, neutralises by the portionwise addition of sodium hydrogen carbonate, extracts 5 times with 1000 ml. amounts of chloroform and evaporates the chloroform extracts, dries over anhydrous sodium sulphate, under reduced pressure almost to dryness. The so obtained mixture of mono- and dinitrate is, after dissolving in 250 ml. ether, extracted 10 times with 100 ml. amounts of water. The aqueous phases contain the mononitrate (RF=0.47; silica gel finished plate, chloroform/methanol 9/1), the dinitrate (Rf=0.75) remaining in the ether phase. From the aqueous phase, one obtains, after saturation with sodium chloride, 5 times extraction with 200 ml. amounts of chloroform and evaporation of the chloroform extracts under reduced pressure, 32.1 g. (0.17 mol) 1.4;3.6-dianhydro-L-iditol 2-nitrate in the form of a colourless oil which is used for the following esterification without further purification.

(b) 1.4;3.6-Dianhydro-L-iditol 2-nitrate 5-nicotinate:

A mixture of 150 ml. anhydrous pyridine, 9.5 g. (50 mmol) 1.4;3.6-dianhydro-L-iditol 2-nitrate and 7.7 g. (55 mmol) nicotinic acid chloride is stirred for 24 hrs. at 20° with the exclusion of moisture. One evaporates off the pyridine under reduced pressure (10 mbar), neutralises the residue with aqueous sodium hydrogen carbonate solution, again evaporates under reduced pressure and extracts the residue with boiling chloroform. Evaporation of the chloroform extract, dried over anhydrous sodium sulphate, and recrystallisation from methanol gives 11.8 g. (40 mmol) 1.4;3.6-dianhydro-L-iditol 2-nitrate 5-nicotinate M.p. 81°–3°; $[\alpha]_D^{25}$ 111 (c 2.0; chloroform)

Elementary analysis: $C_{12}H_{12}N_2O_7$ (296.24): calc.: C, (48.65); H, (4.08); N, (9.46). found: C, (48.85); H, (4.15); N, (9.42).

EXAMPLE NO. 3

1.4;3.6-Dianhydro-L-iditol 2-nitrate 5nicotinate:

(a) 1.4;3.6-Dianhydro-L-iditol 5-nicotinate:

A mixture of 45 g. (0.2 mol) 1.4;3.6-dianhydro-D-glucitol 5-methanesulphonate (prepared according to Example 1a), 32 g. (0.22 mol) sodium nicotinate and 500 ml. anhydrous dimethylformamide is stirred for 15 hrs. at 150°. One distils off the solvent, dissolves the residue in 200 ml. water, adds 5 g. active charcoal thereto and filters. The filtrate is adjusted to pH 8–9 with dilute aqueous sodium hydroxide solution and extracted 3 times with 200 ml. amounts of chloroform. The combined chloroform extracts are extracted 3 times with 200 ml. amounts of 0.25 molar hydrochloric acid, the combined hydrochloric acid extracts are, after washing with 200 ml. chloroform, evaporated under reduced pressure and dried azeotropically with ethanol/chloroform. Recrystallisation of the residue from ethanol/isopropanol gives 17.4 g. (60.6 mmol) crystalline 1.4;3.6-dianhydro-L-iditol 5-nicotinate hydrochloride.

M.p. 148°–50°; $[\alpha]_D^{25}$ 52.6 (c 1.0; water).

Elementary analysis: $C_{12}H_{13}NO_5 \cdot xHCl$ (287.70): calc.: C, (50.10); H, (4.90); N, (4.87); Cl, (12.32). found: C, (50.03); H, (4.88); N, (4.87); Cl, (11.8).

(b) 1.4;3.6-Dianhydro-L-iditol 2-nitrate 5-nicotinate:

To a solution of 3.5 g. (58 mmol) urea in 50 ml. 95% nitric acid one adds dropwise, with stirring and cooling to −20°, a solution of 14 g. (56 mmol) 1.4;3.6-dianhydro-L-iditol 5-nicotinate (free base of the previously obtained hydrochloride) in 30 ml. methanesulphonic acid, stirs for 1 hr. at −20°, pours into 200 ml. ice water and adds dropwise, with cooling, 65 g. sodium hydroxide, dissolved in 200 ml. water. By the addition of sodium hydrogen carbonate, one completes the neutralisation and extracts 5 times with 100 ml. amounts of chloroform. The combined extracts give, after washing with 100 ml. water, drying over anhydrous sodium sulphate and evaporation under reduced pressure, 10.8 g. (36.5 mmol) 1.4;3.6-dianhydro-L-iditol 2-nitrate 5-nicotinate in the form of a colourless, slowly solidifying oil. One dissolves the oil in chloroform, passes in hydrogen chloride, precipitates out the hydrochloride with ether and recrystallises from isopropanol/ether.

M.p. 151°–2° (decomp.); $[\alpha]_D^{25}$ 77.2 (c 0.5; ethanol)

Elementary analysis: $C_{12}H_{12}N_2O_7 \cdot xHCl$ (332.69) calc.: C, (43.32); H, (3.94); N, (8.42); Cl, (10.66). found: C, (43.55); H, (3.91); N, (8.40); Cl, (10.1).

EXAMPLE NO. 4

1.4;3.6-Dianhydro-D-glucitol 2-nitrate 5-methanesulphonate:

To a solution of 22.4 g. (100 mmol) 1.4;3.6-dianhydro-D-glucitol 5-methanesulphonate (prepared according to Example 1a) in 200 ml. acetic acid and 75 ml. acetic anhydride, one adds dropwise, with stirring and cooling to 10°, a solution of 4.5 ml. (100 mmol) 95% nitric acid in 100 ml. acetic acid and 25 ml. acetic anhydride, stirs for 4 hrs. with gradual warming up to room temperature, adds 1200 ml. water thereto, neutralises portionwise with sodium hydrogen carbonate and extracts 3 times with 300 ml. amounts of chloroform. The chloroform extracts give, after drying over anhydrous sodium sulphate, evaporation under reduced pressure and recrystallisation from chloroform/ether, 22.6 g. (84 mmol) 1.4;3.6-dianhydro-D-glucitol 2-nitrate 5-methanesulphonate.

M.p. 105°–6°; $[\alpha]_D^{25}$ 91 (c 2.0; chloroform)

Elementary analysis: $C_7H_{11}NO_3S$ (269.24): calc.: C, (31.23); H, (4.12); N, (5.20); S, (11.91). found: C, (31.62); H, (4.20); N, (5.06); S, (12.0).

EXAMPLE NO. 5

1.4;3.6-Dianhydro-D-glucitol 2-nitrate 5-nicotinate:

(a) Esterification of 1.4;3.6-dianhydro-D-glucitol with nicotinic acid:

A solution of 73 g. (500 mmol) 1.4;3.6-dianhydro-D-glucitol in 1500 ml. anhydrous pyridine is mixed portionwise, with stirring, exclusion of moisture and cooling to 10°, with a total of 72 g. (500 mmol) nicotinic acid chloride and stirred at 50°–60° until reaction of the acid chloride is complete (about 8 hours). One distils off the pyridine under reduced pressure, adjusts the residue to pH=8 with aqueous sodium carbonate solution, again evaporates under reduced pressure and extracts the residue 3 times with 400 ml. amounts of boiling chloroform. The combined chloroform extracts are concentrated to a volume of 500 ml. and subjected to a 40 stage Craig's countercurrent partitioning with water (+1% ethanol) as mobile upper phase. The individual fractions are characterised thin layer chromatographically (silica gel F 254 finished plate, chloroform/methanol 9/1), combined according to the component materials and evaporated. One obtains from the Fractions 1–3: 48.5 g. (136 mmol) 1.4;3.6-dianhydro-D-glucitol 2,5-dinicotinate (Rf=0.49). M.p., after recrystallisation from chloroform/ether: 142°–4° (lit.: British Pat. No. 1,027,891; m.p. 143.5°–144°);

$[\alpha]_D^{25}$ 30.0 (c 2.0; chloroform). (lit.: 28.8; chloroform)

Elementary analysis: $C_{18}H_{16}N_2O_6$ (356.34): calc.: C, (60.67); H, (4.53); N, (7.86). found: C, (60.82); H, (4.55); N, (7.84).

Fractions 4–14: 18.6 g. (74 mmol) 1.4;3.6-dianhydro-D-glucitol 2-nicotinate (Rf=0.32). M.p., after recrystallisation from chloroform/petroleum ether: 112°–113.5°; $[\alpha]_D^{25}$ 69.8 (c 2.0; chloroform)

Elementary analysis: $C_{12}H_{13}NO_5$ (251.24): calc.: C, (57.37); H, (5.21); N, (5.58). found: C, (56.93); H, (5.22); N, (5.47).

Fractions 15–19: 4.5 g. (18 mmol) of a mixture of 1.4;3.6-dianhydro-D-glucitol 2- and 5-nicotinate.

Fractions 20–36: 30.6 g. (122 mmol) 1.4;3.6-dianhydro-D-glucitol 5-nicotinate (Rf=0.25). M.p., after recrystallisation from chloroform/ether: 84°–85.5°; $[\alpha]_D^{25}$ 55.4 (c 2.0; chloroform).

Elementary analysis: $C_{12}H_{13}NO_5$ (251.24): calc.: C, (57.37); H, (5.21); N, (5.58). found: C, (57.60); H, (5.29); N, (5.56).

Fractions 37–40 contain unreacted 1.4;3.6-dianhydro-D-glucitol.

(b) 1.4;3.6-Dianhydro-D-glucitol 2-nitrate 5-nicotinate:

To a solution of 25 g. (100 mmol) of the previously obtained 1.4;3.6-dianhydro-D-glucitol 5-nicotinate in 300 ml. acetic acid and 70 ml. acetic anhydride is slowly added dropwise, with stirring and cooling to 10°, a solution of 6.6 ml. (150 mmol) 95% nitric acid in 100 ml. acetic acid and further stirred for 3 hrs. at this temperature. One dilutes with 1500 ml. water, neutralises by the portionwise addition of sodium hydrogen carbonate and extracts 4 times with 500 ml. amounts of ethyl acetate. The combined extracts give, after washing with aqueous sodium hydrogen carbonate solution, drying over anhydrous sodium sulphate and evaporation under reduced pressure and recrystallisation from methanol/water, 23.7 g. (80 mmol) 1.4;3.6-dianhydro-D-glucitol 2-nitrate 5-nicotinate.

M.p. 107°–108.5°; $[\alpha]_D^{25}$ 58.0 (c 2.0; chloroform)

Elementary analysis: $C_{12}H_{12}N_2O_7$ (296.24): calc.: C, (48.65); H, (4.08); N, (9.46). found: C, (48.55); H, (3.98); N, (9.47).

EXAMPLE NO. 6

1.4;3.6-Dianhydro-D-glucitol 2-nicotinate 5-nitrate:

12.5 g. (50 mmol) of the 1.4;3.6-dianhydro-D-glucitol 2-nicotinate obtained according to Example 5(a) are reacted with nitric acid/acetic anhydride/acetic acid and give, after recrystallisation from chloroform/ether, 10.7 g. (36 mmol) 1.4;3.6-dianhydro-D-glucitol 2-nicotinate 5-nitrate.

M.p. 54°–7°; $[\alpha]_D^{25}$ 117.2 (c 2.0; chloroform)

Elementary analysis: $C_{12}H_{12}N_2O_7$ (296.24): calc.: C, (48.65); H, (4.08); N, (9.46). found: C, (48.73); H, (4.11); N, (9.40).

EXAMPLE NO. 7

1.4;3.6-Dianhydro-D-glucitol 2-nicotinate 5-nitrate:

(a) 1.4;3.6-Dianhydro-D-glucitol 2- and 5-nitrate:

To a solution of 30 g. (200 mmol) 1.4;3.6-dianhydro-D-glucitol in 300 ml. acetic acid and 70 ml. acetic anhydride one adds dropwise, with stirring and cooling to 8°, a solution of 7 ml. (100 mmol) 65% nitric acid in 50 ml. acetic acid and then stirs for 4 hrs. One dilutes with 1000 ml. water and extracts 3 times with 500 ml. amounts of ethyl acetate. The combined extracts are deacidified, with stirring, by the portionwise addition of aqueous sodium hydrogen carbonate solution. One separates off the ethyl acetate phase, dries over anhydrous sodium sulphate and concentrates under reduced pressure to about 50 ml. The concentrate is separated column chromatographically over 1 kg. silica gel with toluene/ethyl acetate 1/1 as eluent.

The fractions with Rf=0.26 (silica gel F 254 finished plate: toluene/ethyl acetate 1/1) give, after evaporation under reduced pressure and recrystallisation from ether, 2.6 g. (13.6 mmol) 1.4;3.6-dianhydro-D-glucitol 2-nitrate.

M.p. 53°–55.5° (lit.: L. D. Hayward et al., Can. J. Chem., 45, 2191–4, 1967, m.p. 52°–3°); $[\alpha]_D^{25}$ 76.4 (c 2.0; chloroform).

Elementary analysis: $C_6H_9NO_6$ (191.15): calc.: C, (37.70); H, (4.74); N, (7.33). found: C, (37.83); H, (4.85); N, (7.25).

The fractions with Rf=0.20 give, after evaporation under reduced pressure and recrystallisation from ethyl acetate/petroleum ether, 8.8 g. (46 mmol) 1.4;3.6-dianhydro-D-glucitol 5-nitrate. M.p. 86°–88° (lt.: 85.5°–91°); $[\alpha]_D^{25}$ 163.4 (c 2.0; chloroform).

Elementary analysis: $C_6H_9NO_6$ (191.15): calc.: C, (37.70); H, (4.74); N, (7.33). found: C, (37.94); H, (4.88); N, (7.09).

(b) 1.4;3.6-Dianhydro-D-glucitol 2-nicotinate 5-nitrate:

7.65 g. (40 mmol) of the so obtained 1.4;3.6-dianhydro-D-glucitol 5-nitrate are reacted analogously to Example 2(b) with nicotinic acid chloride in pyridine and give, after recrystallisation from chloroform/ether, 9.0 g. (30.4 mmol) 1.4;3.6-dianhydro-D-glucitol 2-nicotinate 5-nitrate.

M.p. 55°–7°; $[\alpha]_D^{25}$ 117 (c 2; chloroform).

EXAMPLE NO. 8

1.4;3.6-Dianhydro-D-mannitol 2-nitrate 5-nicotinate:

To a solution of 10.3 g. (41 mmol) 1.4;3.6-dianhydro-D-mannitol 2-nicotinate in 100 ml. acetic acid, one adds 20 ml. acetic anhydride and 0.6 g. urea, adds dropwise, with stirring and cooling to 10°, a solution of 8.8 g. (200 mmol) 96% nitric acid in 20 ml. acetic acid and leaves to stir overnight at room temperature. One then pours, with stirring, into 500 ml. ice water, stirs for ½ hour and neutralises by the addition of 500 ml. 20% aqueous sodium hydroxide solution, with cooling, and subsequently by the addition of sodium hydrogen carbonate. Precipitated product is thereby brought into solution by the addition of some chloroform. The mixture is extracted 4 times with 200 ml. amounts of chloroform. The combined chloroform extracts give, after washing with 200 ml. water, drying over anhydrous sodium sulphate and evaporation under reduced pressure, oily crude product from which, after recrystallisation from isopropanol and subsequently from ethanol, one obtains 10.3 g. (34.8 mmol) pure 1.4;3.6-dianhydro-D-mannitol 2-nitrate 5-nicotinate. M.p. 132°–134°; $[\alpha]_D^{25}$ 264.3 (c 0.5; chloroform).

Elementary analysis: $C_{12}H_{12}N_2O_7$ (296.24): calc.: C, (48.65); H, (4.08); N, (9.46). found: C, (48.70); H, (4.27); N, (9.59).

In the case of the investigation of the pharmacological properties of the compounds according to the invention, as comparison compounds there were always used the commercially available compounds isosorbide dinitrate (ISDN) and isosorbide mononitrate (ISMN), whereby ISMN is 1.4;3.6-dianhydro-D-glucitol 2-nitrate.

The coronary flowthrough-increasing effectiveness of the compounds according to the invention was determined on isolated guinea pig hearts (isolated hearts according to Langendorff, method according to Bunger et al., Pflüger's Archiv, 353, 317–325 (1975)). After achieving the stationary state in the 30th minute, the hearts were each infused with 50 ml. tyrode solution with a content of, in each case, 25 µg./ml. of test substance. Each test substance was tested on 3–6 hearts.

In each case, there were measured the inotropism, the flowthrough and the frequency, whereby the values given in Table I are average values of the percentage changed in comparison with the initial values. The comparison of the measured values shows that the coronary flowthrough-increasing effectiveness of the compounds according to the invention is greater than that of ISMN. Some of the compounds according to the invention show favourable inotropic and frequency-lowering actions.

The spasmolytic effectiveness of the compounds according to the invention was determined on isolated rat aorta preparations with noradrenaline- and potassium chloride-induced contractions (method according to Wende and Peiper, Pflüger's Archiv, 320, 1970, 133-141; and Towart and Stoepel, Naunyn-Schmiedeberg's Archives of Pharmacology; Suppl. Vol. 308, 1979, R 18). Here, too, ISDN and ISMN were chosen as comparison compounds.

In Table II are given the concentrations (molar) of the test substances which are necessary for 50% inhibition of the spasm ($ED_{50}$ values). The spasmolytic effectivenesses of the compounds according to the invention are better than those of ISMN and, in some cases, are better than those of ISDN.

The blood pressure-lowering effectiveness of the compounds according to the invention was measured, in comparison with ISDN and ISMN, on narcotised guinea pigs after i.v. administration. The values given in Table III show that the compounds according to the invention are all more effective than ISMN, whereby the compounds No. 2b and 5b possess actions similar to those of ISDN.

The inotropic and frequency-lowering heart-circulation effectiveness of compound No. 5b according to the invention was, furthermore, determined on mongrel cats of 2.5–3.5 kg. body weight with intraduodenal administration. The animals were narcotised with a mixture of chloralose-urethane (1.2 g./kg. urethane+40 mg./kg chloralose administered i.p.). They breathed spontaneously through a tracheal canula. The A. carotis was used in order to place a catheter tip manometer in the left heart chamber. The V. jugularis served for injection purposes. Via the A. femoralis, a catheter was inserted into the Aorta descendans and attached to a pressure recorder (Statham P 23 Db). The heart frequency was recorded with a pulse frequency measurer (firm Hugo Sachs Elektronik) from the left ventricular pressure signal. A duodenal loop was exposed by laparotomy. The substances to be tested were injected directly into the lumen.

As follows from the values given in Table IV, the blood pressure-lowering action of the tested compound according to the invention is better than that of the comparison compound ISDN.

TABLE I

Experiments on the Langendorff heart
The values given in the Table show the percentage change in comparison with the initial value

| substance | inotropism | flowthrough | frequency |
|---|---|---|---|
| ISMN | +5.40 | +9.70 | +2.42 |
| 1 c | +12.25 | +19.81 | +2.89 |
| 2 b | +3.36 | +35.37 | ±0 |
| 4 | ±0 | +44.26 | ±0 |
| 5 b | +15.77 | +23.55 | −9.13 |

TABLE II

| substance | noradrenaline spasm | potassium chloride spasm |
|---|---|---|
| ISDN | $1.30 \times 10^{-6}$ | $3.10 \times 10^{-6}$ |
| ISMN | $1.60 \times 10^{-5}$ | $2.40 \times 10^{-6}$ |
| 1 c | $1.40 \times 10^{-7}$ | $3.18 \times 10^{-6}$ |
| 2 b | $2.80 \times 10^{-7}$ | $3.10 \times 10^{-6}$ |
| 4 | $2.20 \times 10^{-6}$ | $2.80 \times 10^{-6}$ |
| 5 b | $6.20 \times 10^{-6}$ | $2.25 \times 10^{-5}$ |
| 7 b | $2.00 \times 10^{-5}$ | $4.40 \times 10^{-5}$ |

TABLE III

Blood pressure experiments on the guinea pig (i.v.)

| substance | dose mg/kg | blood pressure previously mm.Hg | blood pressure afterwards mm.Hg | Δ mm.Hg |
|---|---|---|---|---|
| ISDN | 0.25 | 68.70 ± 2.30 | 57.00 ± 2.10 | −11.70 |
|  | 1.00 | 66.00 ± 3.50 | 46.30 ± 0.90 | −19.70 |
|  | 2.50 | 66.70 ± 1.70 | 37.70 ± 0.90 | −29.00 |
| ISMN | 0.25 | 57.60 ± 3.10 | 53.90 ± 3.10 | −3.70 |
|  | 1.00 | 54.70 ± 3.80 | 48.40 ± 3.10 | −6.30 |
|  | 2.50 | 52.30 ± 4.80 | 41.40 ± 3.90 | −10.90 |
| 1 c | 0.25 | 61.30 ± 2.60 | 59.70 ± 2.40 | −1.60 |
|  | 1.00 | 61.90 ± 1.90 | 46.90 ± 1.20 | −15.00 |
|  | 2.50 | 60.60 ± 1.80 | 37.60 ± 1.00 | −23.00 |
| 2 b | 0.25 | 58.70 ± 4.30 | 47.30 ± 2.60 | −11.40 |
|  | 1.00 | 58.30 ± 2.00 | 42.70 ± 1.80 | −15.60 |
|  | 2.50 | 53.70 ± 3.30 | 33.00 ± 1.00 | −20.70 |
| 5 b | 0.25 | 62.70 ± 3.00 | 55.00 ± 1.00 | −7.70 |
|  | 1.00 | 62.30 ± 4.10 | 44.30 ± 0.90 | −18.00 |
|  | 2.50 | 61.30 ± 4.90 | 33.30 ± 0.70 | −28.00 |

TABLE IV

| substance + dose | time (min) after admin. | frequency min$^{-1}$ | blood pressure mm.Hg | Δ | dp/dt mm.sec. | Δ |
|---|---|---|---|---|---|---|
| ISDN | 0 | 174.3 ± 9.3 | 104.3 ± 7.7 |  | 8800 ± 831 |  |
|  |  |  |  | −13.9 |  | −800 |
| 5 mg/kg | 10 | 179.3 ± 7.7 | 90.4 ± 12.5 |  | 8000 ± 1097 |  |
|  |  |  |  | −13.1 |  | −1133 |
|  | 30 | 177.7 ± 7.7 | 91.2 ± 10.0 |  | 7766 ± 807 |  |
|  |  |  |  | −10.1 |  | −1167 |
|  | 60 | 175.0 ± 8.6 | 94.2 ± 9.2 |  | 7633 ± 743 |  |
|  |  |  |  | −9.3 |  | −1750 |
|  | 120 | 166.7 ± 9.4 | 95.0 ± 9.6 |  | 7050 ± 661 |  |
| 5 b | 0 | 211.5 ± 19.3 | 123.5 ± 7.3 |  | 10625 ± 2083 |  |
|  |  |  |  | −25.2 |  | −2575 |
| 5 mg/kg | 10 | 209.5 ± 19.2 | 98.3 ± 6.2 |  | 8050 ± 1204 |  |
|  |  |  |  | −28.7 |  | −2650 |
|  | 30 | 212.5 ± 21.6 | 94.8 ± 7.2 |  | 7975 ± 1216 |  |
|  |  |  |  | −29.7 |  | −2350 |
|  | 60 | 225.0 ± 16.2 | 93.8 ± 7.8 |  | 8275 ± 309 |  |
|  |  |  |  | −22.2 |  | −3125 |
|  | 120 | 228.0 ± 15.6 | 101.3 ± 11.2 |  | 7500 ± 1022 |  | heart frequency (min$^{-1}$), blood pressure (mm.Hg) and inotropism (mm.Hg/sec.) after intraduodenal administration of ISDN or substance No. 5 b to cats.
Average values + standard errors on groups of 6 animals.

For informing examination of acute toxiticity of some of the compounds according to the invention, said compounds were intravenously administered as hydrochlorides in physiological saline solution to female NMRIalbino mice in doses of 100 and 200 mg/kg, respectively. The compounds were injected to at least 3 animals per dose. If no animal had yet been died following to the highest dose which was administered, no more doses of substances were tested. In case of doubt, the examination was repeated with at least 3 more animals applying the same dose.

The rate of death within 24 hours after administration was observed.

In table V, the determined rates of death as well as the $LD_{50}$-ranges evaluated therefrom are shown.

TABLE V

| Compound according to example | Frequency of death with an intravenous dose of | | Evaluated $LD_{50}$-range (mg/kg) |
|---|---|---|---|
| | 200 mg/kg | 100 mg/kg | |
| 2b/3b | 2/6 | 0/6 | ≧200 |
| 5b | — | 0/6 | >100 |
| 6/7b | 0/6 | — | >200 |
| 8 | 3/3 | 0/6 | <200, >100 |

We claim:

1. 2-O- and 5-O-substituted 1.4;3.6-Dianhydrohexitol mononitrates of the general formula I,

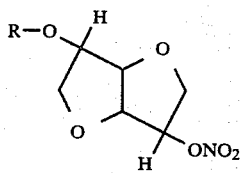

wherein R is a halogen-substituted phenyl group, a methanesulphonyl or nicotinoyl group, as well as their physiologically acceptable acid-addition salts, insofar as R signifies the nicotinoyl group.

2. 5-O-Substituted 1.4;3.6-dianhydro-L-iditol 2-nitrates of the general formula V,

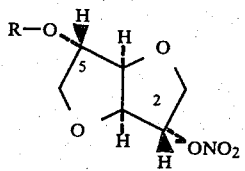

wherein R possesses the meanings given in claim 1, as well as their physiologically acceptable acid-addition salts.

3. 5-O-Substituted 1.4;3.6-dianhydro-D-glucitol 2-nitrates of the general formula VI,

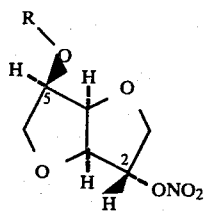

wherein R possesses the meanings given in claim 1, as well as their physiologically acceptable acid-addition salts.

4. 2-O-Substituted 1.4;3.6-dianhydro-D-glucitol 5-nitrates of the general formula VII,

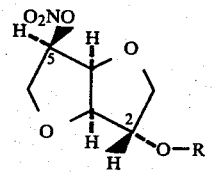

wherein R possesses the meanings given in claim 1, as well as their physiologically acceptable acid-addition salt.

5. 5-O-Substituted 1.4;3.6-dianhydro-D-mannitol 2-nitrates of the general formula VIII,

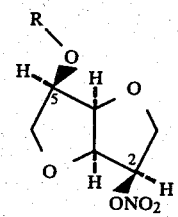

wherein R possesses the meanings given in claim 1, as well as their physiologically acceptable acid-addition salts.

6. 5-O-(4-Chlorophenyl)-1.4;3.6-dianhydro-L-iditol 2-nitrate.

7. 1.4;3.6-Dianhydro-L-iditol 2-nitrate 5-nicotinate.

8. 1.4;3.6-Dianhydro-D-glucitol 2-nitrate 5-methanesulphonate.

9. 1.4;3.6-Dianhydro-D-glucitol 2-nitrate 5-nicotinate.

10. 1.4;3.6-Dianhydro-D-glucitol 2-nicotinate 5-nitrate.

11. 1.4;3.6-Dianhydro-D-mannitol 2-nitrate 5-nicotinate.

12. 1.4;3.6-Dianhydro-D-mannitol 2-nitrate 5-methanesulphonate.

13. A pharmaceutical composition comprising the compound of claim 1, 2, 3, 4, 5, 6, 7, 8, 9, 10, 11 or 12, and a pharmaceutically acceptable carrier therefore.

14. A method for the treatment of coronary diseases in humans comprising administering a pharmacologically effective amount of the composition of claim 13.

* * * * *